(12) United States Patent
Walulik et al.

(10) Patent No.: US 6,277,119 B1
(45) Date of Patent: Aug. 21, 2001

(54) EXTERNAL FIXATION SYSTEM

(75) Inventors: Stephen B. Walulik, Phillipsburg; Kirk J. Bailey, Blairstown; Sean P. Curry, Hoboken; John Scott Mahaffey, Hackettstown, all of NJ (US)

(73) Assignee: Electro-Biology, Inc., Parsippany, NJ (US)

( * ) Notice: Subject to any disclaimer, the term of this patent is extended or adjusted under 35 U.S.C. 154(b) by 0 days.

(21) Appl. No.: 09/422,377

(22) Filed: Oct. 21, 1999

(51) Int. Cl.[7] .................................................. A61B 17/56
(52) U.S. Cl. .................................. 606/57; 606/56; 606/59
(58) Field of Search ............................. 606/54, 55, 56, 606/57, 58, 59

(56) References Cited

U.S. PATENT DOCUMENTS

| 2,391,537 | * | 12/1945 | Anderson . | |
| 2,391,693 | * | 12/1945 | Ettinger | 606/57 X |
| 4,258,708 | * | 3/1981 | Gentile . | |

(List continued on next page.)

FOREIGN PATENT DOCUMENTS

| 2033758 | * | 5/1980 | (GB) | 606/54 |
| 780838 | * | 11/1980 | (SU) | 606/59 |

OTHER PUBLICATIONS

Howmedica, Inc. manual entitled "External Fixation of a Complex Femoral Fracture, Frame Construction Manual", copyright 1981, 24 pages.
Howmedica brochure entitled "Howmedica Trauma Simple Solutions", copyright 1998, 26 pages.
Synthes brochure entitled "The AO/ASIF Hybrid Fixator Technique Guide", copyright 1995, 25 pages.

*Primary Examiner*—Jeffrey A. Smith
(74) *Attorney, Agent, or Firm*—Harness, Dickey & Pierce, P.L.C.

(57) ABSTRACT

An external fixation system for securing a first bone portion in a fixed relationship with respect to a second bone portion. The fixation system includes at least one cylindrical support rod and a plurality of universal clamp assemblies for engagement with at least one support rod. The fixation system additionally includes various other distinct components for interconnecting the support rod with bone pins engaged with the bone. Some of the other components are formed to include serrations for engaging corresponding serrations provided on the universal clamp assemblies. Some of the components include a cylindrical portion, whereas other of the components include a rod receiving portion adapted to receive the at least one support rod or one of the cylindrical portions. These interchangeable and distinct components allow for a greater degree of surgeon flexibility in producing a desired construction to secure bone portions with bone pins.

20 Claims, 12 Drawing Sheets

U.S. PATENT DOCUMENTS

| | | | |
|---|---|---|---|
| 4,488,542 | 12/1984 | Helland | 128/92 A |
| 4,553,273 | 11/1985 | Wu | 623/18 |
| 4,600,000 | 7/1986 | Edwards | 128/92 |
| 4,657,550 | 4/1987 | Daher | 623/17 |
| 4,662,365 | 5/1987 | Gotzen et al. | 128/92 ZW |
| 5,211,664 | 5/1993 | Tepic et al. | 623/16 |
| 5,261,912 | 11/1993 | Frigg | 606/61 |
| 5,352,224 | 10/1994 | Westermann | 606/61 |
| 5,403,315 | 4/1995 | Ashman | 606/61 |
| 5,451,225 | 9/1995 | Ross, Jr. et al. | 606/59 |
| 5,454,810 * | 10/1995 | Pohl et al. | 606/59 |
| 5,520,689 | 5/1996 | Schlapfer et al. | 606/61 |
| 5,527,311 | 6/1996 | Procter et al. | 606/61 |
| 5,534,002 | 7/1996 | Brumfield et al. | 606/61 |
| 5,542,946 | 8/1996 | Logroscino et al. | |
| 5,562,662 | 10/1996 | Brumfield et al. | 606/61 |
| 5,601,552 | 2/1997 | Cotrel | 606/61 |
| 5,624,440 | 4/1997 | Huebner | 606/59 |
| 5,643,258 | 7/1997 | Robioneck et al. | 606/54 |
| 5,676,666 | 10/1997 | Oxland et al. | 606/61 |
| 5,683,389 | 11/1997 | Orsak | 606/59 |
| 5,683,390 | 11/1997 | Metz-Stavenhagen et al. | 606/61 |
| 5,688,272 | 11/1997 | Montague et al. | 606/61 |
| 5,688,274 | 11/1997 | Errico et al. | 606/61 |
| 5,702,393 | 12/1997 | Pfaifer | 606/61 |
| 5,709,681 | 1/1998 | Pennig | 606/54 |
| 5,741,252 | 4/1998 | Mazzio et al. | 606/54 |
| 5,741,254 | 4/1998 | Henry et al. | 606/61 |
| 5,743,911 | 4/1998 | Cotrel | 606/61 |
| 5,746,741 | 5/1998 | Kraus et al. | 606/54 |
| 5,752,954 | 5/1998 | Mata et al. | 606/59 |
| 5,782,833 | 7/1998 | Haider | 606/61 |
| 5,827,283 * | 10/1998 | Groiso et al. | 606/57 |
| 5,863,293 | 1/1999 | Richelsoph | 606/61 |
| 5,888,221 | 3/1999 | Gelbard | 623/17 |
| 5,891,144 | 4/1999 | Mata et al. | 606/59 |
| 5,921,985 | 7/1999 | Ross, Jr. et al. | 606/59 |
| 5,961,515 | 10/1999 | Taylor et al. | 606/59 |
| 5,997,537 * | 12/1999 | Walulik | 606/56 |
| 6,080,153 * | 6/2000 | Mata et al. | 606/59 X |

* cited by examiner

EXTERNAL FIXATION SYSTEM

BACKGROUND OF THE INVENTION

1. Field of the Invention

The present invention relates generally to an orthopedic surgical procedure, and more particularly to an external fixation system for bones.

2. Description of the Related Art

In various orthopedic surgical procedures, it is often necessary to secure two or more portions of bone in a relatively fixed relationship to each other. This need is often a result of a fracture which has occurred to the bone. To ensure that the bone can properly regenerate and fuse the fractures of the bone, it is important that the various bone portions be fixed at the desired position during bone regeneration.

Various external fixation devices for the repair of traumatized bone are known. For example, commonly assigned U.S. Pat. No. 5,620,442 to Bailey et al. discloses an apparatus for the external fixation of small bones. The apparatus is illustrated to include a bone screw clamp for receiving a first bone screw which is connected to a first bone portion. The external fixator further includes a bone screw clamp which is operable to receive a second bone screw connected to the second bone portion. The first and second bone screw clamps include a spherical portion. The external fixator further includes a connection member for securing the spherical portions of the bone screw clamps. The connection member defines a radiographic window to permit radiographic examination of the bone fracture without removing the apparatus. U.S. Pat. No. 5,620,442 is hereby incorporated by reference as if fully set forth herein.

While known fixators, including the type described above, have proven to be effective in fixating bones, they nevertheless can be the subject of certain improvements. In this regard, conventional external fixation devices often do not provide the flexibility required for particular applications. Thus, it would be advantageous to provide an external fixation system with a plurality of interchangeable and distinct components which allow for a greater degree of surgeon flexibility in producing a desired construction.

SUMMARY OF THE PRESENT INVENTION

According to one aspect of the present invention, the invention relates to an external fixation system operable for securing two portions of bone in a fixed relationship to each other including various interchangeable components which can be selected by a surgeon.

An advantage of the present invention is to provide an external fixation system for bones and a related method that permit independent placement of bone pins at various positions and angular orientations along a bone.

Another advantage of the present invention is to provide an external fixation system for bones and a related method that incorporate a universal base clamp which can be placed any free space along a support rod without requiring the removal of other elements that may be secured to the support rod.

Another advantage of the present invention is to provide an external fixation system for bones and a related method that include a compression/distraction arrangement for relatively translating a pair of spaced apart support rods.

Another advantage of the present invention is to provide an external fixation system for bones and a related method that include a telescoping bone screw clamp that allows a surgeon to displace a bone pin from a support rod.

Another advantage of the present invention is to provide an external fixation system for bones and a related method that include a plurality of distinct components including cooperating serrated portions for facilitating interconnection between the components.

A related advantage of the present invention is to provide an external fixation system for bones and a related method that include a plurality of distinct components each including one of a cylindrical rod and a rod receiving portion to facilitate interconnection between the components and a cylindrical support rod.

Additional advantages and features of the present invention will become apparent from the following description and appended claims, taken in conjunction with the accompanying drawings.

DETAILED DESCRIPTION OF THE PREFERRED EMBODIMENT

The following description of the preferred embodiment of the present invention is merely exemplary in nature and is in no way intended to limit the invention or its application or uses.

Figure 1A:
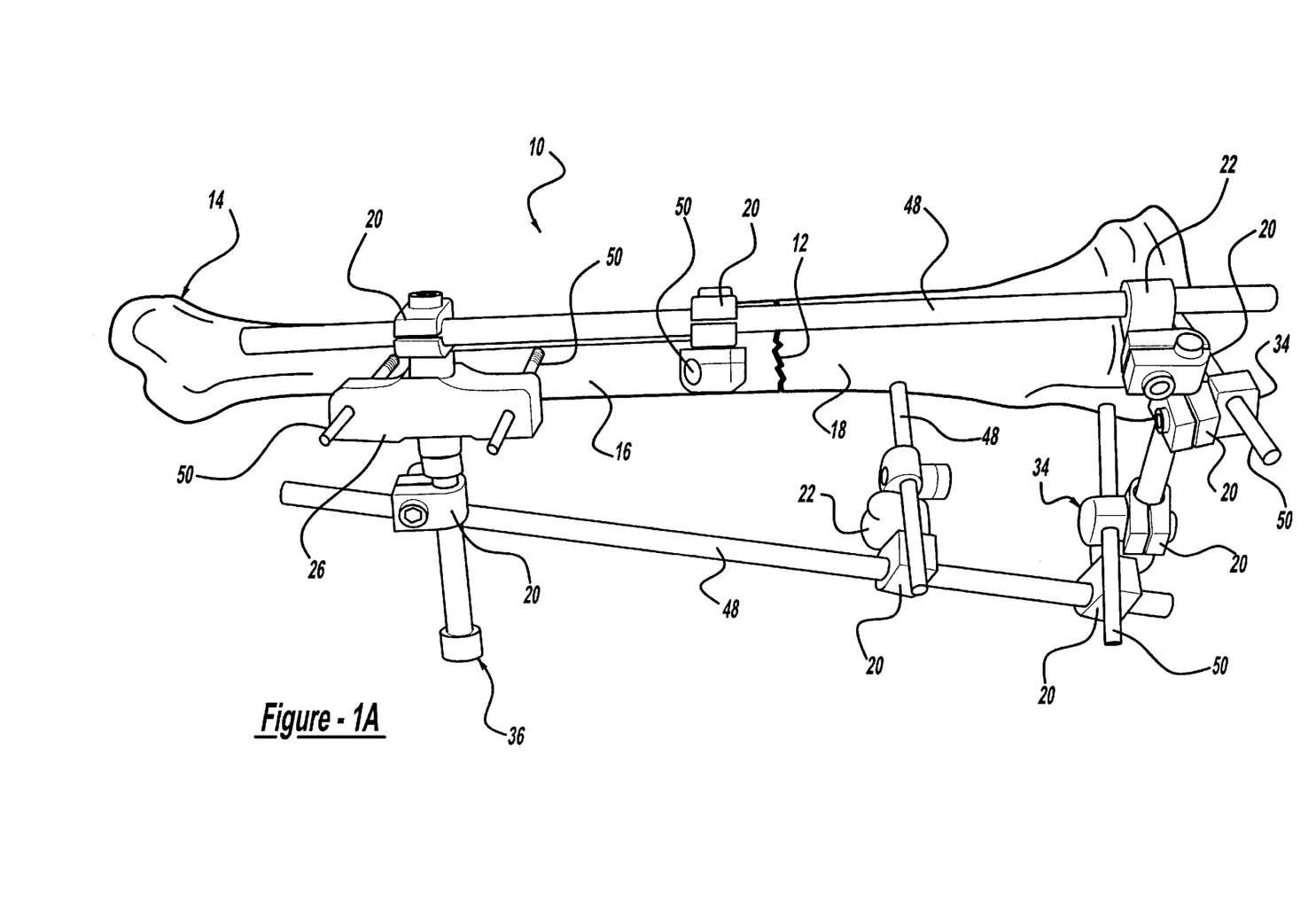
FIGS. 1A and 1B illustrate a first exemplary construct of components of the external fixation system according to the teachings of the preferred embodiment of the present invention in operative association with a tibia.
Figure 1B:
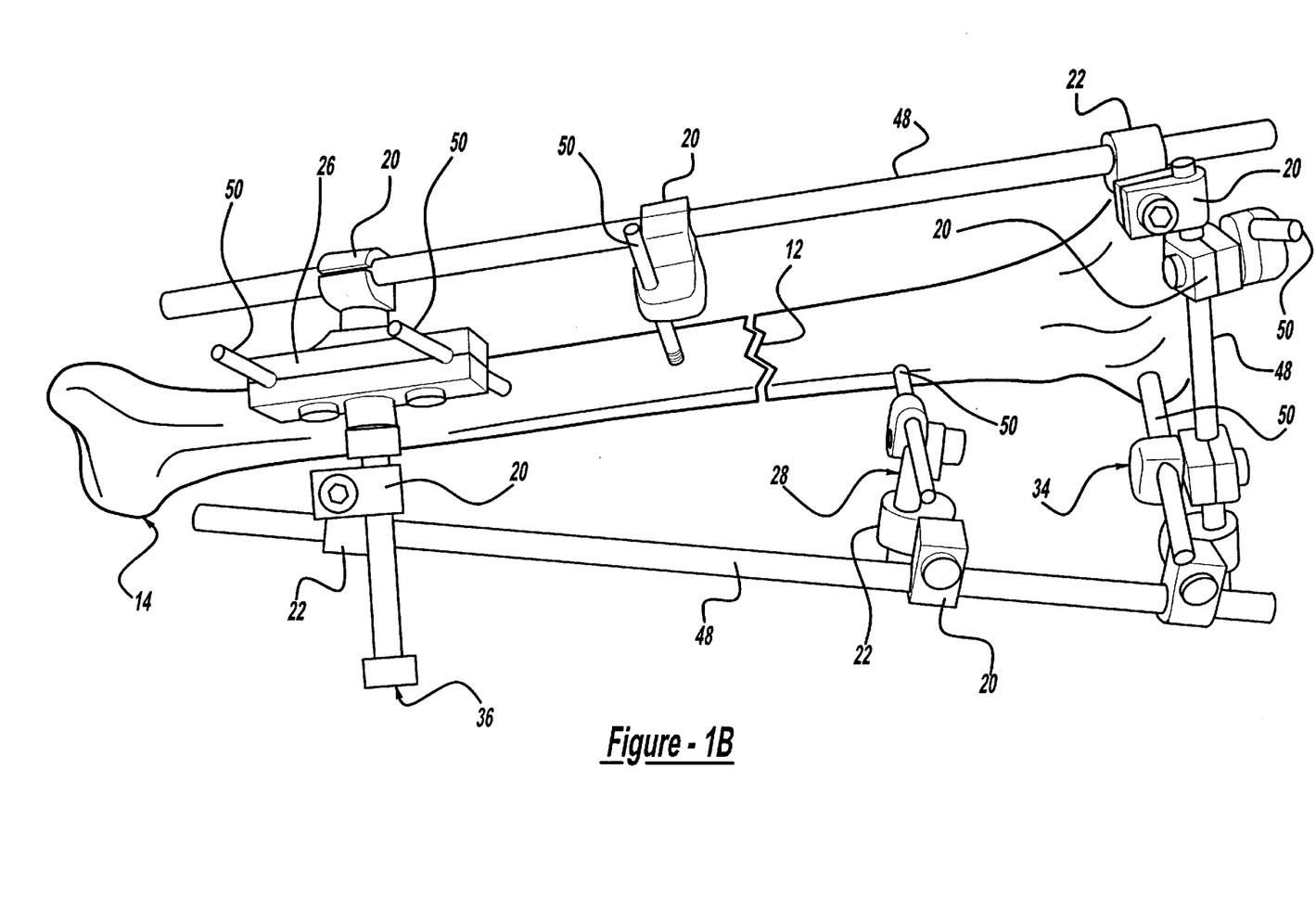
Figure 2:
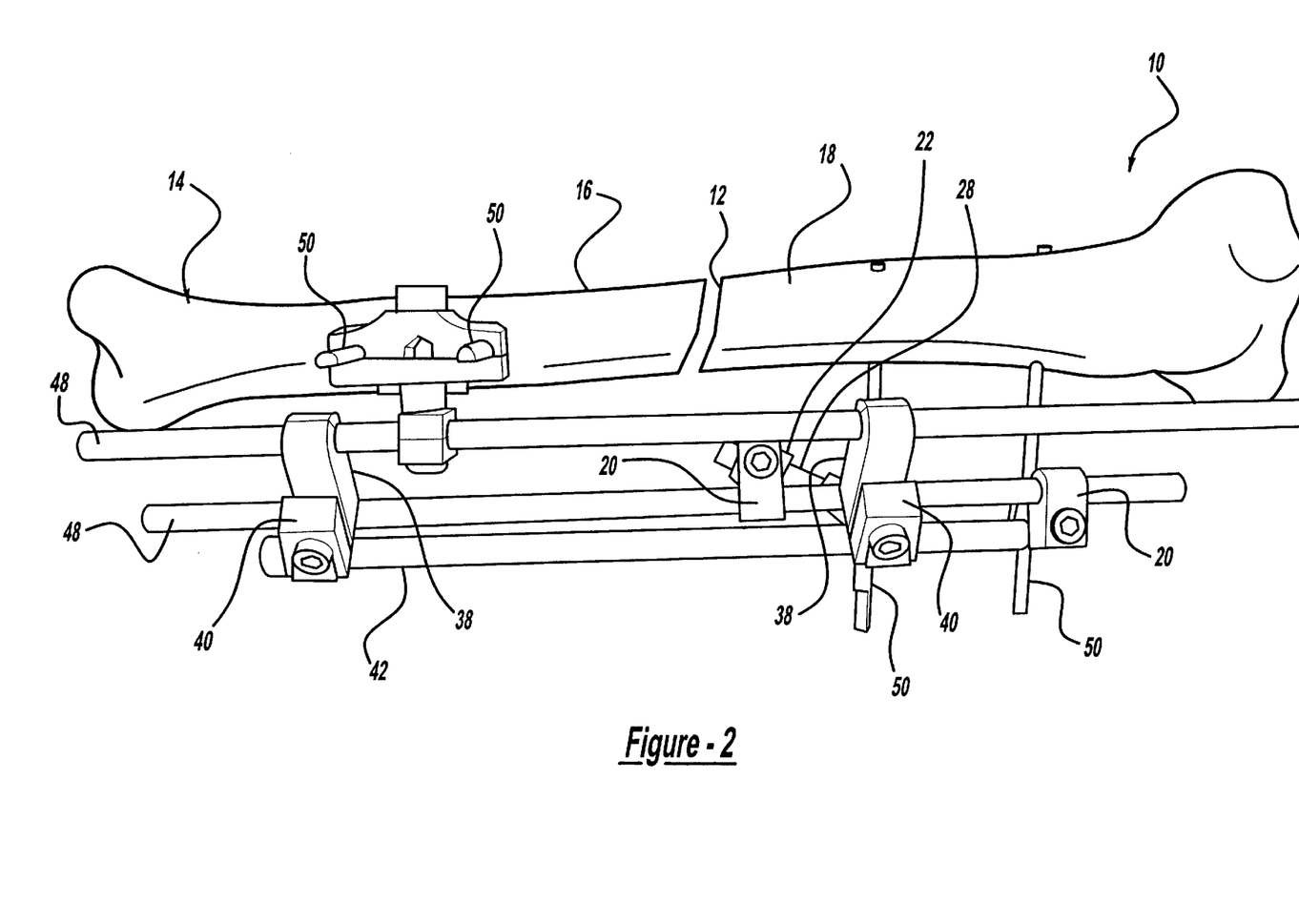
FIG. 2 illustrates a second exemplary construct of components of the external fixation system according to the teachings of the preferred embodiment of the present invention in operative association with a tibia, the second construct incorporating a compression/distraction arrangement.
Figure 3A:
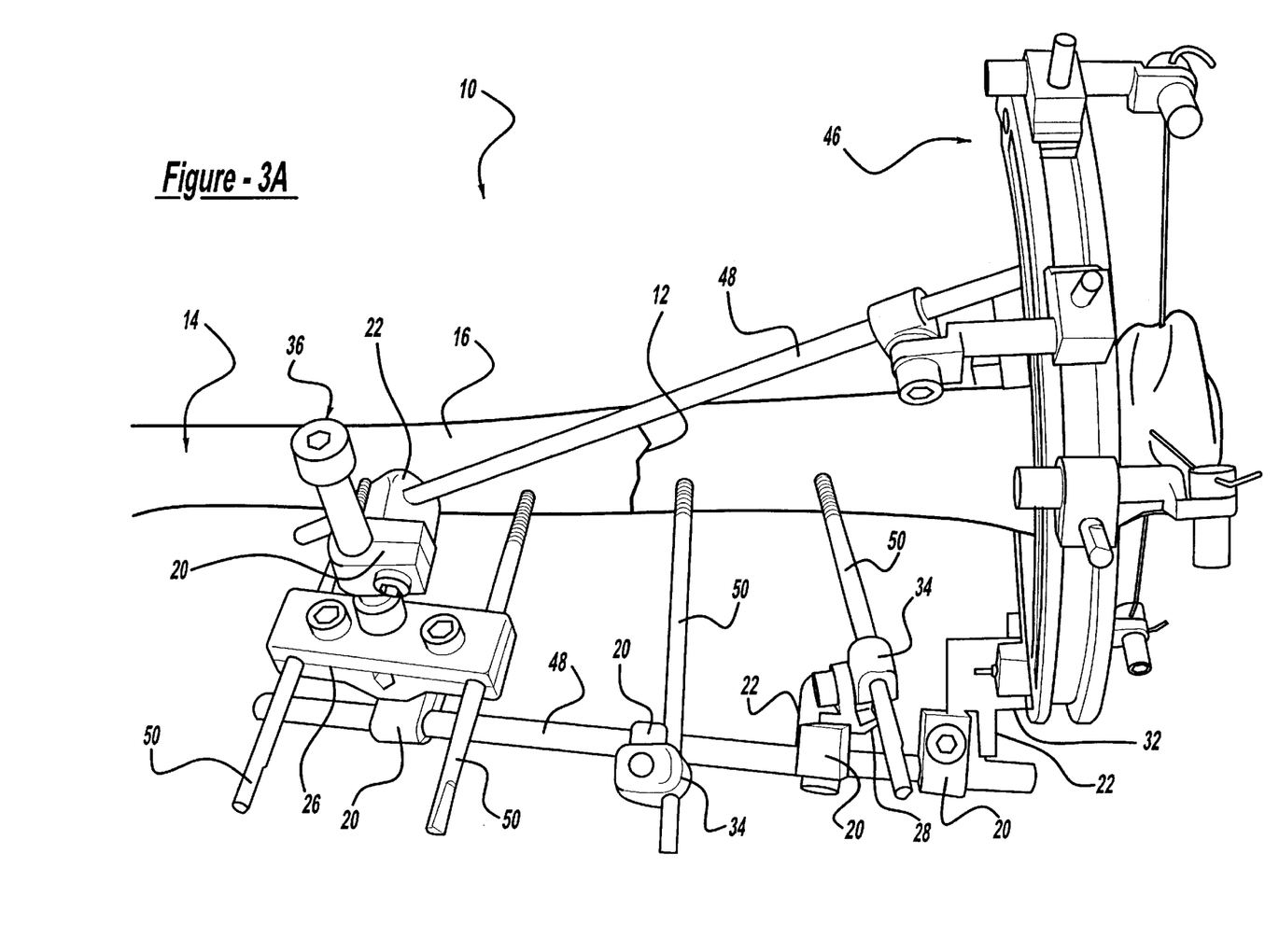
FIGS. 3A and 3B illustrate a third exemplary construct of components of the external fixation system according to the teachings of the preferred embodiment of the present invention in operative association with a tibia, the third construct incorporating a ring assembly.
Figure 3B:
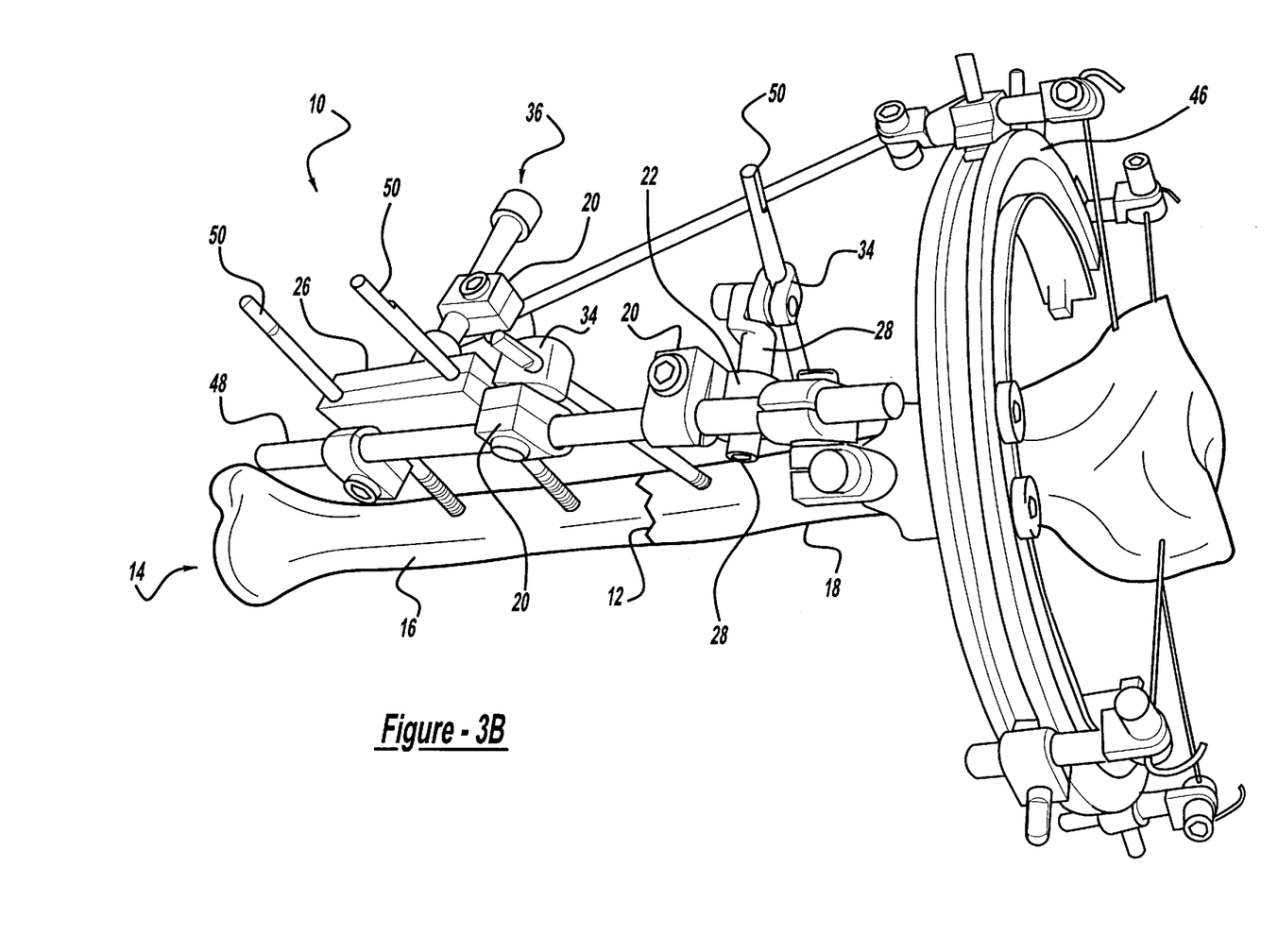

Referring initially to FIGS. 1 through 3, illustrated are three constructs of cooperating components of the system 10 for external fixation of bone according to the preferred embodiment of the present invention. In FIGS. 1A and 1B, a first construct of components of the system 10 is shown securing a fracture 12 of a bone 14. In particular, the system 10 is illustrated as being used to secure a bone fracture 12 of a tibia 14. The system 10 is used to secure the bone portions 16 and 18 in a fixed relationship so as to permit the fractured portions to fuse properly. FIG. 2 illustrates a second construct of the system 10 shown operatively attached to the tibia 14. In FIG. 3, a third construct of the system 10 is illustrated attached to the tibia 14. While the system 10 is shown throughout FIGS. 1 through 3 in conjunction with a tibia 14, it will be appreciated that the system 10 may be used with other bones as well. It will also be appreciated that the three constructions illustrated in FIGS. 1 through 3 are merely exemplary applications.

The structure and function of the individual cooperating components of the system 10 will be described with general reference to FIGS. 1 through 15. The components of the present invention are illustrated to generally include a universal clamp assembly 20, bar-to-bar clamp body 22, a three pin clamp assembly 24, a five pin clamp assembly 26, a telescoping post 28, a first ring connector assembly 30, a second ring connector assembly 32, a bone pin clamp body 34, and a post assembly 36. The components are illustrated to additionally include a compression/distraction arrangement 38 including a pair of clamping assemblies 40 and an externally threaded drive rod 42. Further, the components include a variable connector body 44, a ring assembly 46, and a plurality of cylindrical, smooth support rods 48. The support rods 48 include main support rods which are typically oriented to extend generally parallel to the axis of the bone 14 or at an acute angle relative to the bone 14 and supplemental support rods. The supplemental support rods 48', one of which is shown in FIG. 1B, may be provided in various lengths.

As will become apparent below, the components of the system 10 of the present invention may be combined in an infinite number of combinations and orientations to secure and rigidly interconnect a plurality of bone screws or pins 50 which are engaged with the bone portions 16 and 18. This flexibility of the system 10 permits a surgeon to independently place a bone 50 at a limitless number of positions along the bone 14 or angular orientations with respect to the bone 14.

Figure 4A:
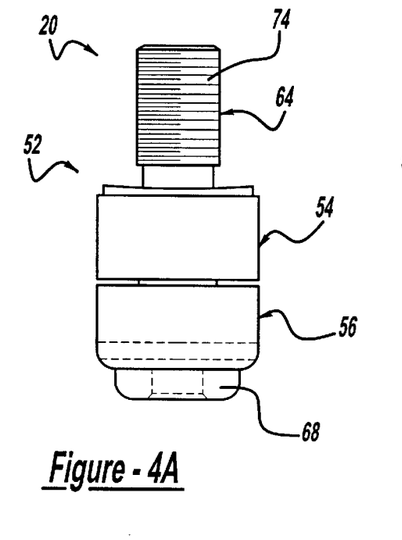
FIGS. 4A and 4B are views of a universal clamp assembly of the external fixation system according to the teachings of the preferred embodiment of the present invention.
Figure 4B:
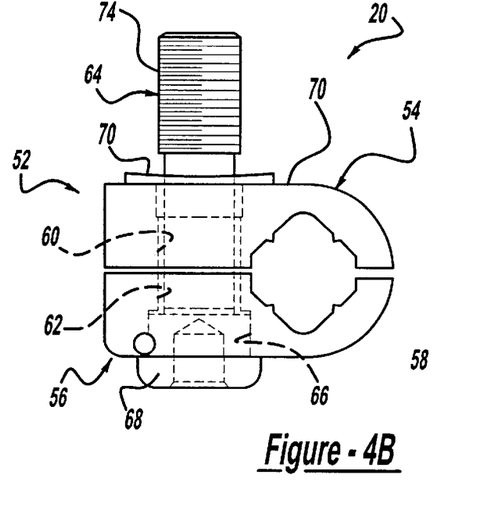

With reference to FIGS. 4A and 4B, the universal clamp assembly 20 of the present invention is illustrated. The universal clamp assembly 20 includes a clamp portion 52 having first and second halves 54 and 56 which cooperate to define a bar receiving aperture 58 for receiving one of the support rods 48, the telescoping post 28 or the post assembly 36. It will be understood that in the exemplary embodiment the support rods 48, telescoping post 28 and post assembly 36 each have a substantially identical diameter.

The first and second halves 54 and 56 include aligning apertures 60 and 62, respectively, for receiving a locking bolt or fastener 64. The aperture 62 of the second half 56 includes a counterbored portion 66 for receiving a portion of a head 68 of the fastener 64. An outer surface 70 of the first half 54 is formed to include a serrated portion 72 having a plurality of serrations radially extending from the opening of the aperture 60. The serrated portion 72 is adapted to engage substantially identical serrated portions provided on cooperating components of the system 10 of the present invention as will be discussed below.

An end 74 of the fastener 64 opposite the head 68 is externally threaded. When the fastener 64 engages an internally threaded aperture of a cooperating component and is rotated to draw the cooperating component against the first half 56, the first and second halves 56 of the clamp portion 52 are drawn together to thereby securely clamp one of the support rods 48, for example, within the aperture 58. The rod receiving aperture 58 is sized to receive one of the support rods 48, the telescoping post 28 or the post assembly 36.

The universal base clamp 20 is the fundamental component of the system 10 of the present invention. The universal base clamp 20 is designed to be easily placed anywhere along a support rod 48, for example (even between two previously locked universal base clamps 20). This can be cone by sliding the first half 54 up the fastener 64 and then rotating the first half 54 ninety degrees. This feature allows a surgeon to add components during the application without the inconvenience of unlocking clamps 20 already in place.

Figure 5A:
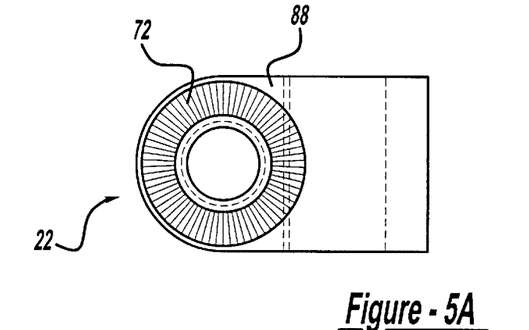
FIGS. 5A through 5C are views of a bar-to-bar clamp body of the external fixation system according to the teachings of the preferred embodiment of the present invention.
Figure 5B:
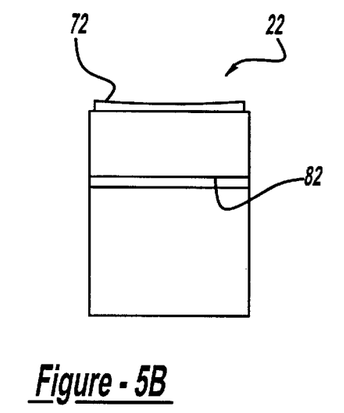
Figure 5C:
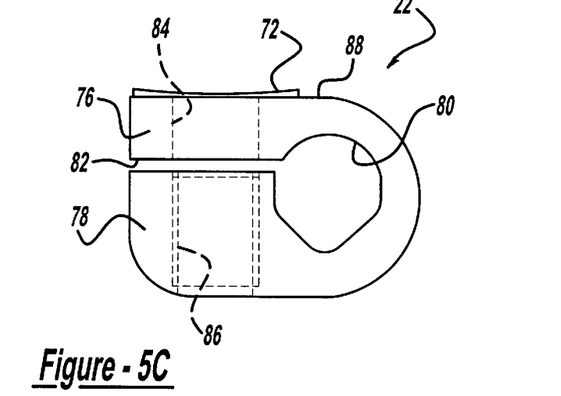

With reference to FIGS. 5A through 5C, the bar-to-bar clamp body 22 of the present invention is illustrated. The bar-to-bar clamp body 22 is generally C-shaped to define a rod receiving aperture 80 and includes first and second ends 76 and 78 which are spaced apart by an opening 82. The first and second ends 76 and 78 include aligning apertures 84 and 86, respectively, for receiving a fastener such as the fastener 64 described above with respect to the universal clamp assembly 20. The aperture 86 of the second end 78 is internally threaded. An outer surface 88 of the first end 76 is formed to include a serrated portion 72.

In use, the bar-to-bar clamp body 22 is attached to a cooperating component of the system 10 of the present invention through engagement of the fastener 64 with the apertures 84 and 86. In such engagement, the serrated portions 72 of the components are interlocked thereby preventing relative rotation. Tightening of the fastener 64 draws the ends 76 and 78 of the bar-to-bar clamp body 22 toward one another. As a result, a support rods 48, telescoping post 28 or post assembly 36 positioned within the aperture 80 is secured relative to the bar-to-bar clamp body 22 and in turn secured relative to the cooperating component.

Figures 6A, 6B:
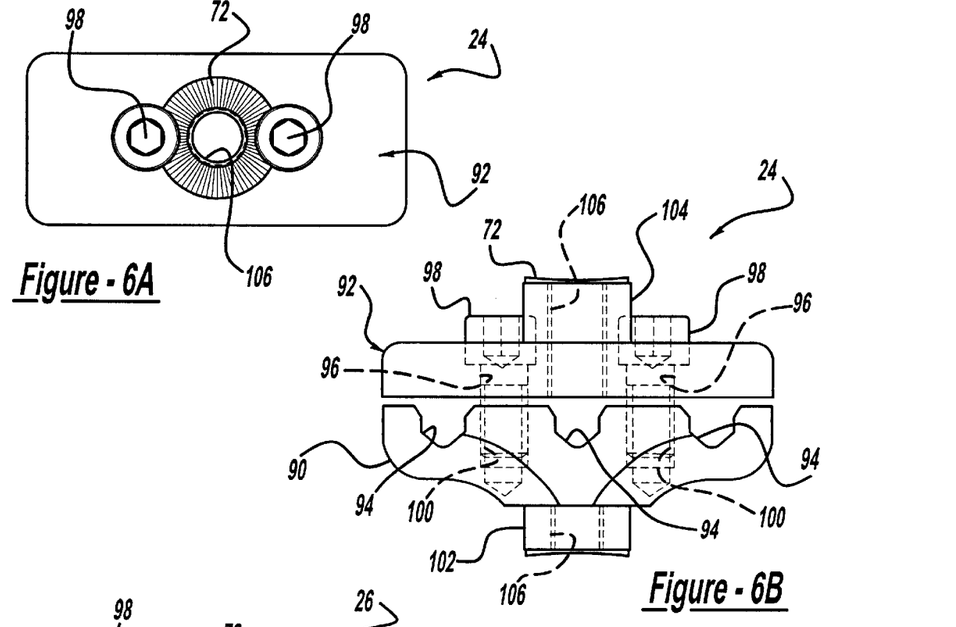
FIGS. 6A and 6B are views of a three pin clamp assembly of the external fixation system according to the teachings of the preferred embodiment of the present invention.

With reference to FIGS. 6A and 6B, the three pin clamp assembly 24 of the present invention is illustrated. The pin clamp assembly 24 is operative for receiving and securing up to three bone pins 50 engaged with the bone 14. The bone pin clamp 28 includes a main body member 90 and a cover member 92. The main body member 90 defines three bone pin rests 94. The bone pin rests or grooves 94 are substantially V-shaped and are operable to engage the sides of the bone pins 50.

The cover member 92 of the pin clamp assembly 24 is able to be inserted over the bone pins 50 when the bone pins 50 are located in the grooves 94. The cover member 92 includes a pair of apertures 96 which each allow a threaded fastener 98 to pass through the cover member 32 and into a threaded aperture 100 of the main body member 90. Tightening of the fasteners 98 rotationally and longitudinally secures the bone pins 50 relative to the pin clamp assembly 24.

To facilitate secure attachment of the pin clamp assembly 24 to other cooperating components of the system 10 of the present invention, the base member 90 and the cover member 92 are both formed to integrally include cylindrical extensions 102 and 104, respectfully. The ends of each of the cylindrical extensions 102 and 104 are both formed to include a serrated portion 72. Each of the cylindrical extensions 102 and 104 includes an internally threaded aperture 106 sized to receive a fastener 64.

Figure 7A:
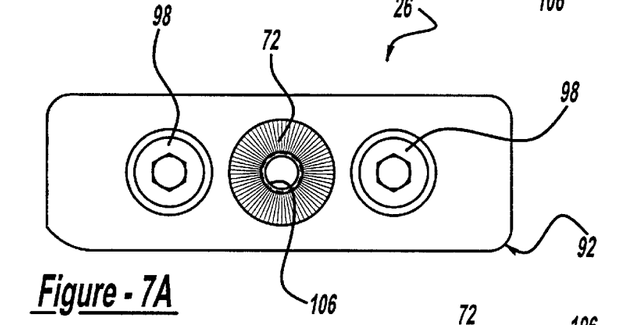
FIGS. 7A and 7B are views of a five pin clamp assembly of the external fixation system according to the teachings of the preferred embodiment of the present invention.
Figure 7B:
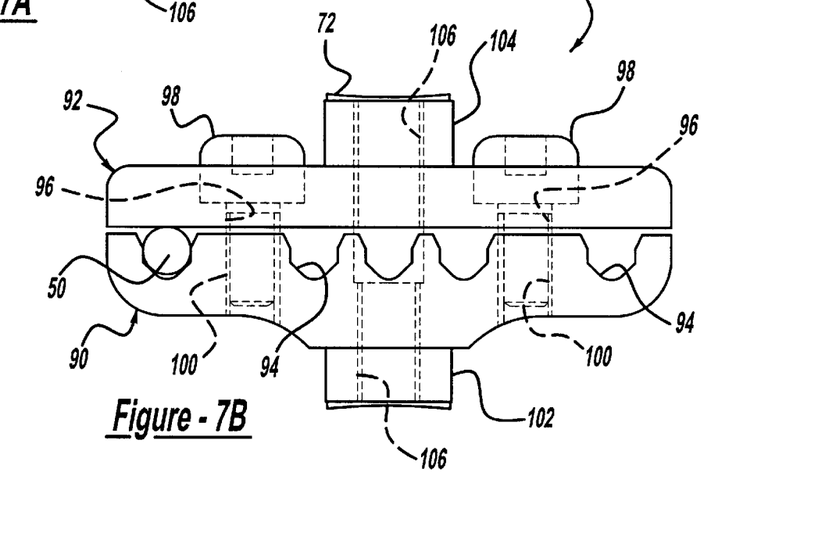

The five pin clamp assembly 26 is shown particularly in FIGS. 7A and 7B. The construction of the five pin clamp assembly 26 is identical to the construction of the three pin clamp assembly 26, with the exception that the five pin clamp assembly 26 is formed to include two additional bone pin rests 94. In this regard, the five pin clamp assembly 26 includes three bone pin rests 94 between the fasteners 98, whereas the three pin clamp assembly 24 includes a single bone pin rest 94 between the fasteners. Due to the similarity between the two pin clamp assemblies 24 and 26, like reference numbers are used in the drawings.

Figure 8A:
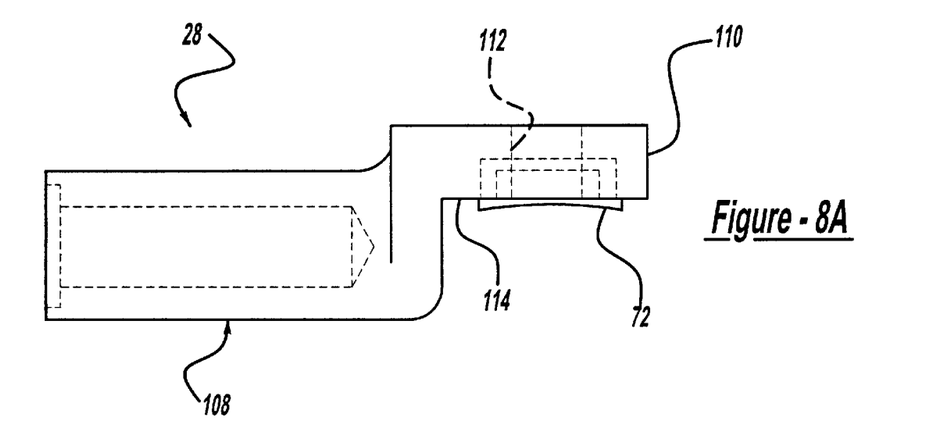
FIGS. 8A and 8B are views of a telescoping post of the external fixation system according to the teachings of the preferred embodiment of the present invention.
Figure 8B:
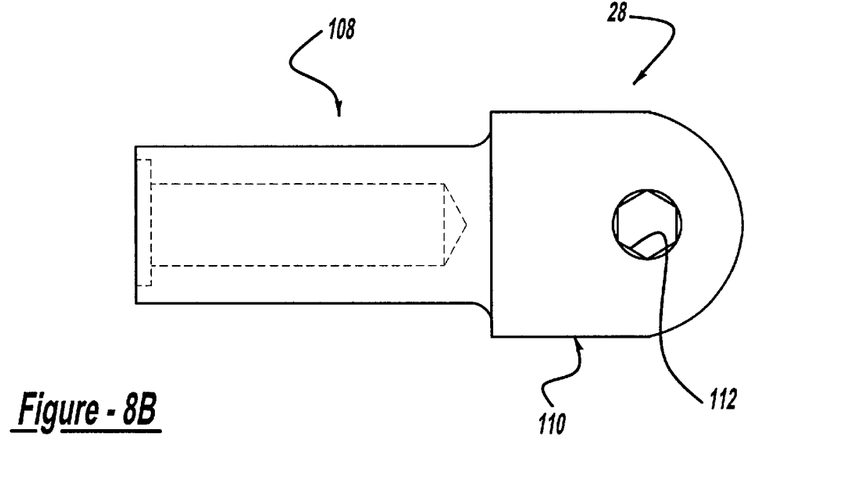

Turning now to FIGS. 8A and 8B, the telescoping post 28 of the present invention is illustrated. The telescoping post 28 includes a cylindrical post portion 108 and a mounting flange portion 110. The cylindrical post portion 108 has a diameter substantially equal to the diameter of the support rods 48 and thereby may be securely received within rod receiving apertures of cooperating components of the system 10 of the present invention. The mounting flange portion 110 includes an aperture 112 for receiving a fastener 64. A lower side 114 of the mounting flange portion 110 includes a serrated portion 72 for cooperating with the serrated portions of cooperating components of the system 10 in a manner discussed above.

Figure 9A:
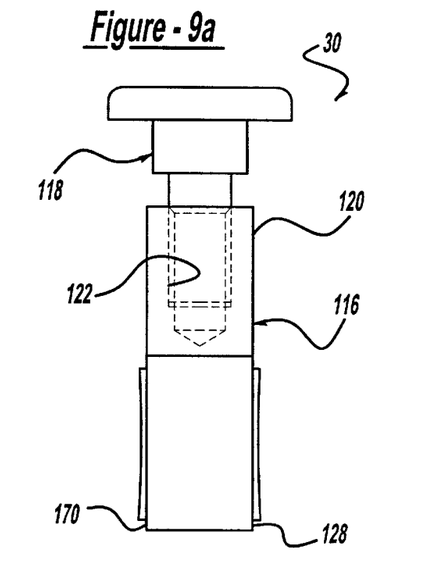
FIGS. 9A and 9B are views of a first ring connector assembly of the external fixation system according to the teachings of the preferred embodiment of the present invention.
Figure 9B:
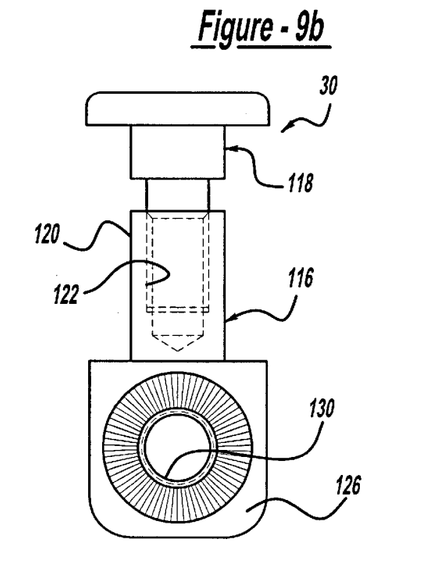

With reference to FIGS. 9A and 9B, the first ring connector assembly 30 of the present invention is illustrated.

The first ring connector assembly includes a main body 116 and a fastener 118. An upper portion 120 of the main body 116 defines a vertically extending aperture 122 which is internally threaded to receive the externally threaded fastener 118. A lower portion 124 of the main body 116 includes a pair of spaced apart sides 126 and 128 and an aperture 130 horizontally passing therethrough. Both of the sides 126 and 128 are formed to include a serrated portion 72 radially surrounding the aperture 130 which is adapted to interface with cooperating components of the system 10 including a serrated portion 72 in a manner discussed above. The fastener 118 is adapted to pass through one of a plurality of apertures formed in a frame 132 of the ring assembly 46 for securing the first ring connector assembly 32 thereto.

Figure 10A:
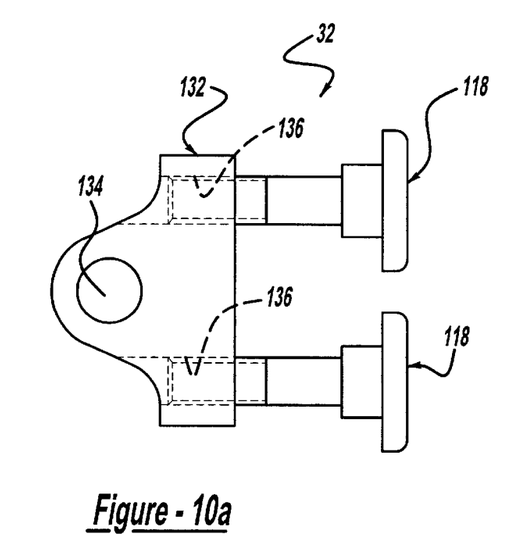
FIGS. 10A and 10B are views of a second ring connector assembly of the external fixation system according to the teachings of the preferred embodiment of the present invention.
Figure 10B:
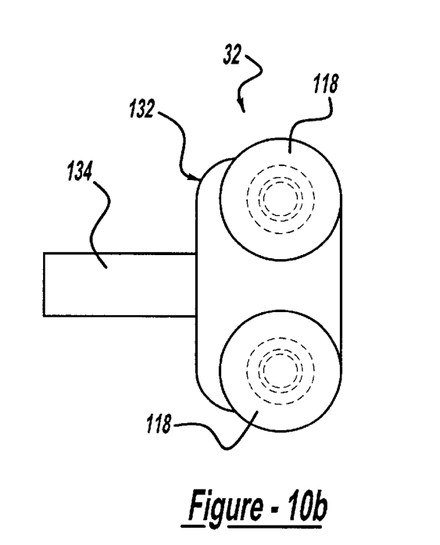
Figures 11A, 11B, 11D:
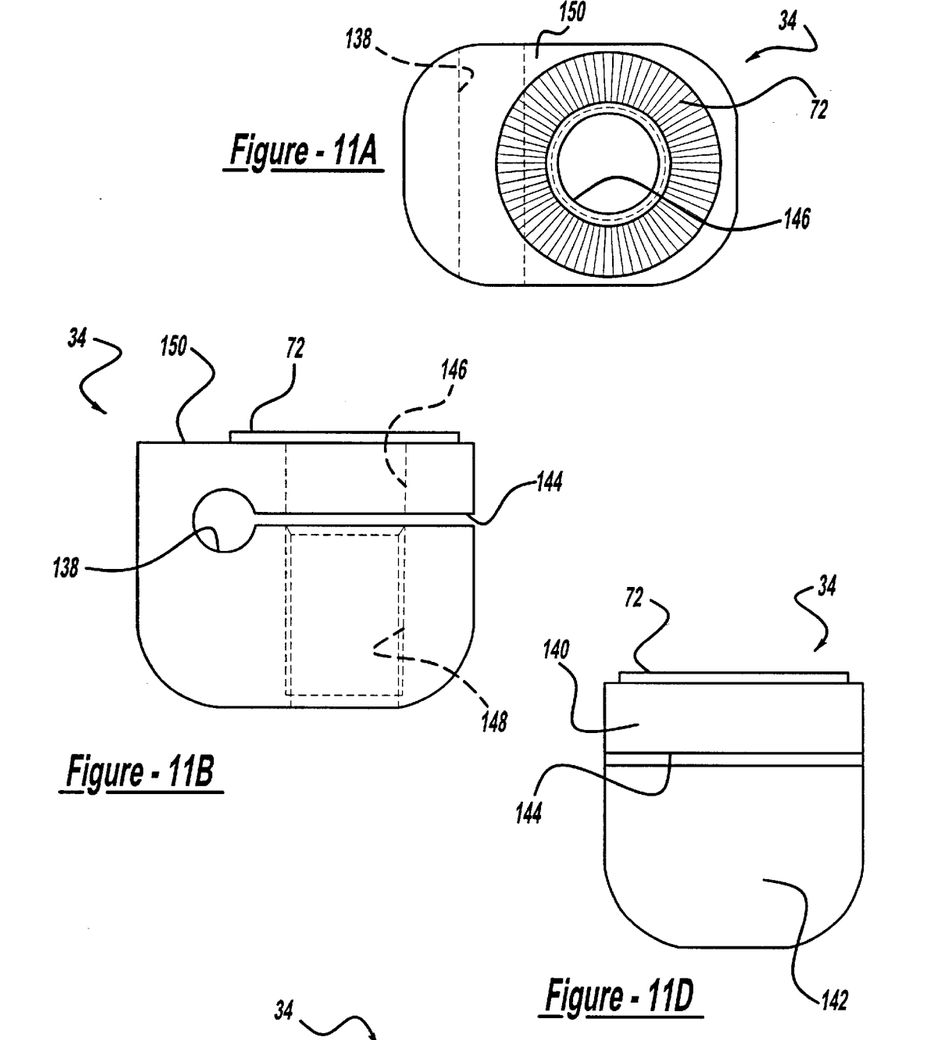
FIGS. 11A through 11D are views of a bone pin clamp body of the external fixation system according to the teachings of the preferred embodiment of the present invention.
Figure 11C:
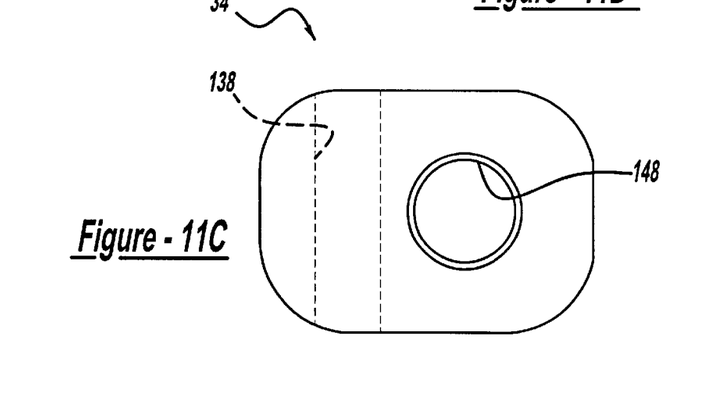

With reference to FIGS. 10A and 10B, the second ring connector assembly 32 of the present invention is illustrated. Rather than interfacing with cooperating components of the system 10 including a serrated portion 72, the second ring connector assembly 32 is adapted to interface with cooperating components including a rod receiving aperture, such as the universal clamp assembly 20 and the bar-to-bar clamp body 22. The second ring connector assembly 32 includes a main body portion 132 and a cylindrical extension 134. To facilitate clamping within one of the rod receiving apertures, the cylindrical extension 134 has a diameter substantially equal to the support rods 48. The main body 132 defines a pair of apertures 136 which are internally threaded for receiving a pair of threaded fasteners 118 identical to the fastener described with respect to the first ring connector assembly 30. In a similar manner, the fasteners 118 are adapted to pass through a pair of the plurality of apertures formed in the frame 132 of the ring assembly 46 for securing the second ring connector assembly thereto.

With reference to FIGS. 11A through 11D, the bone pin clamp body 34 of the present invention is illustrated. The bone pin clamp body 34 defines an aperture 138 for receiving a bone pin 50. The pin clamp body 34 includes an upper flange portion 140 and a lower flange portion 142 which are separated by a gap 144. The gap 144 intersects the aperture 138. The upper and lower flange portions 140 and 142 are formed to include aligning apertures 146 and 148 for receiving a fastener 64. The aperture 148 of the lower flange portion 142 is internally threaded.

An upper surface 150 of the upper flange portion 140 includes a serrated portion 72 surrounding the aperture 146. The serrated portion 72 is adapted to interface with serrated portions of cooperating components of the system 10 of the present invention in a manner discussed above. When a cooperating component is secured to the bone pin clamp body 34 with a fastener 64, tightening of the fastener 64 causes the gap 144 between the upper and lower flange portions 140 and 142 to decrease and the aperture 138 to slightly constrict. As a result, a bone pin 50 disposed within the aperture 138 is longitudinally and rotationally fixed with respect to the bone pin clamp body 34.

Figures 12A, 12B, 12C:
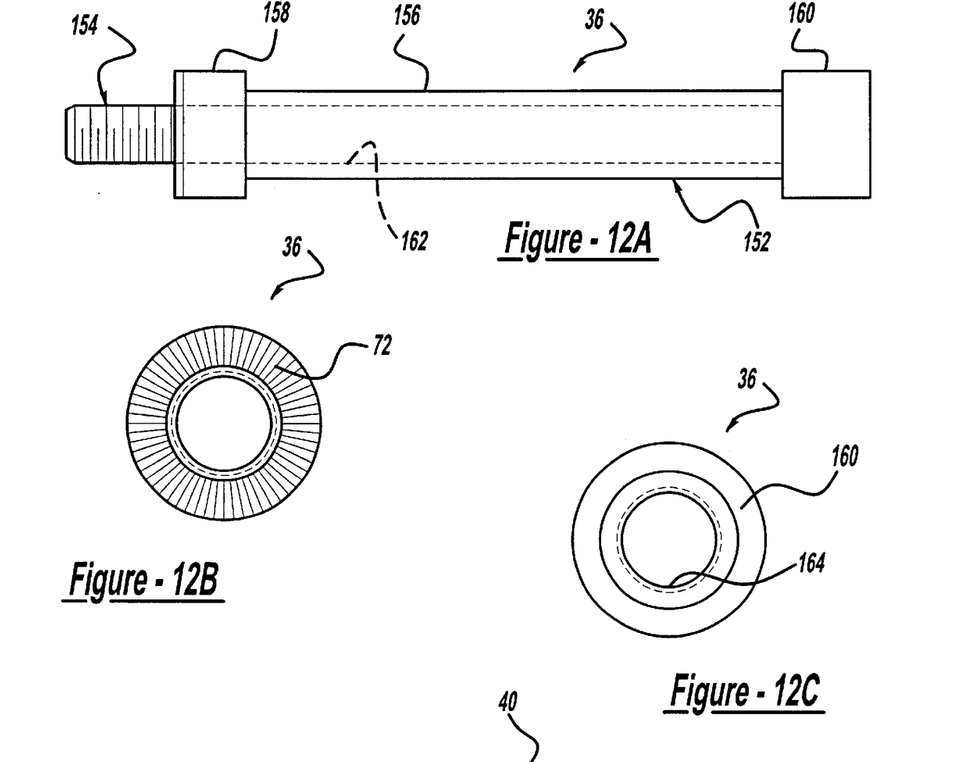
FIGS. 12A through 12C are views of a post assembly of the external fixation system according to the teachings of the preferred embodiment of the present invention.

Turning now to FIGS. 12A through 12C, the post assembly 36 of the present invention is illustrated. The post assembly 36 generally includes a cylindrical sleeve 152 and a threaded fastener 154. The cylindrical sleeve 152 includes a central portion 156 and first and second enlarged ends 158 and 160. The cylindrical sleeve 152 has a diameter substantially equal to the diameter of the support rods 48 and can similarly interface with cooperating components including a rod receiving aperture, such as the universal clamp assembly 20, in a manner discussed above.

The cylindrical sleeve 152 defines an elongated aperture 162 for receiving the fastener 154. An outer end of the first enlarged end 158 includes a serrated portion 72 surrounding the aperture 162. The fastener 154 extends beyond the serrated portion and is externally threaded. An opposite end of the fastener 154 includes a recess 164 for receiving a tool (not shown) used to rotate the fastener 154 relative to the cylindrical sleeve 152. The serrated portion 72 is adapted to interface with serrated portions 72 of cooperating components of the system 10 of the present invention in a manner discussed above. The serrated portion 72 is particularly intended to cooperate with the 3 pin and 5 pin clamp assemblies.

Figures 14A, 14B:
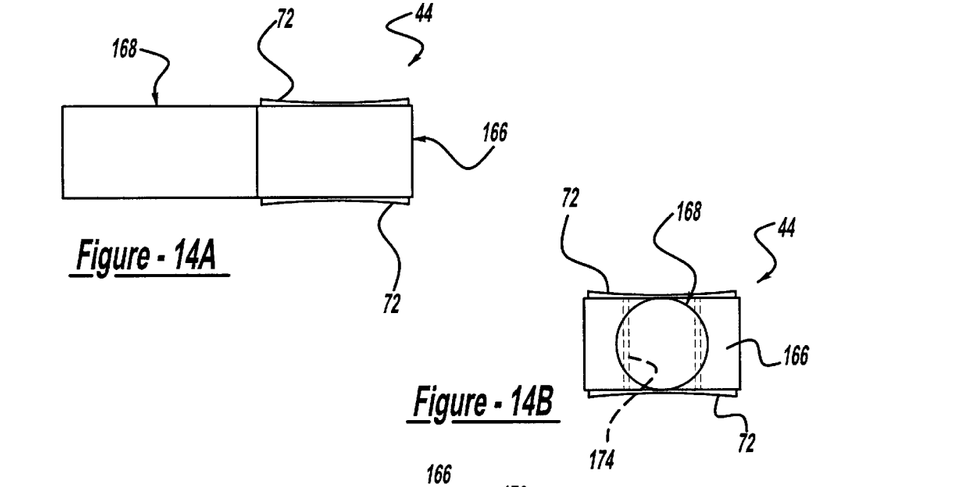
FIGS. 14A through 14C are views of a variable connector body of the external fixation system according to the teachings of the preferred embodiment of the present invention.
Figure 14C:
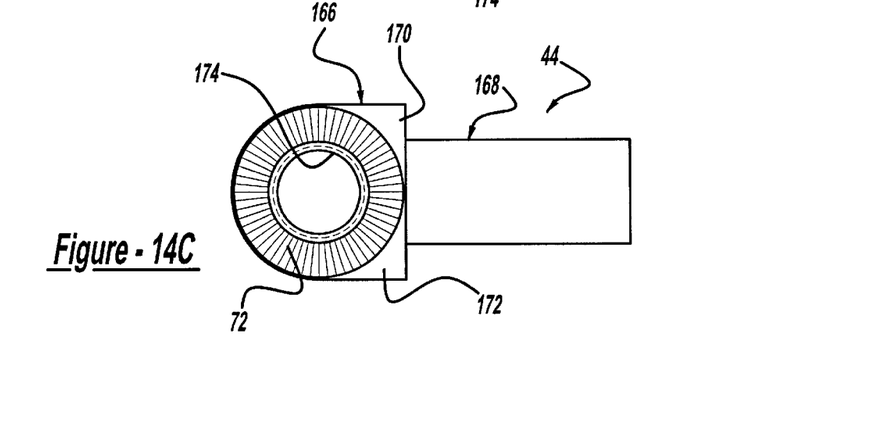

With reference to FIGS. 14A through 14C the variable connector body 44 of the present invention will be described. The variable connector body 44 generally includes a main body 166 and a cylindrical portion 168 extending from the main body 166. The main body 166 includes a pair of spaced apart sides 170 and 172 and an internally threaded aperture 174 passing therethrough. Both of the sides 170 and 172 are formed to include a serrated portion 72 radially surrounding the aperture 174 which is adapted to interface with cooperating components of the system 10 including a serrated portion 72 in a manner discussed above. The cylindrical portion 168 has a diameter substantially equal to the diameter of the support rods 48 and thereby may be securely received within rod receiving apertures of cooperating components of the system 10 of the present invention in a manner discussed above.

Figure 13:
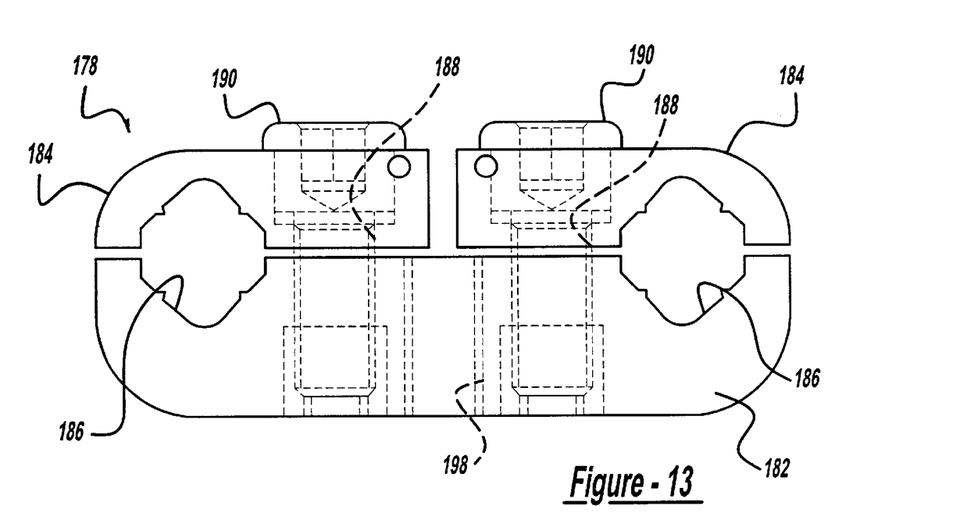
FIG. 13 is a side elevational view a bar clamping unit of a compression/distraction arrangement of the external fixation system according to the teachings of the preferred embodiment of the present invention.
Figure 15:
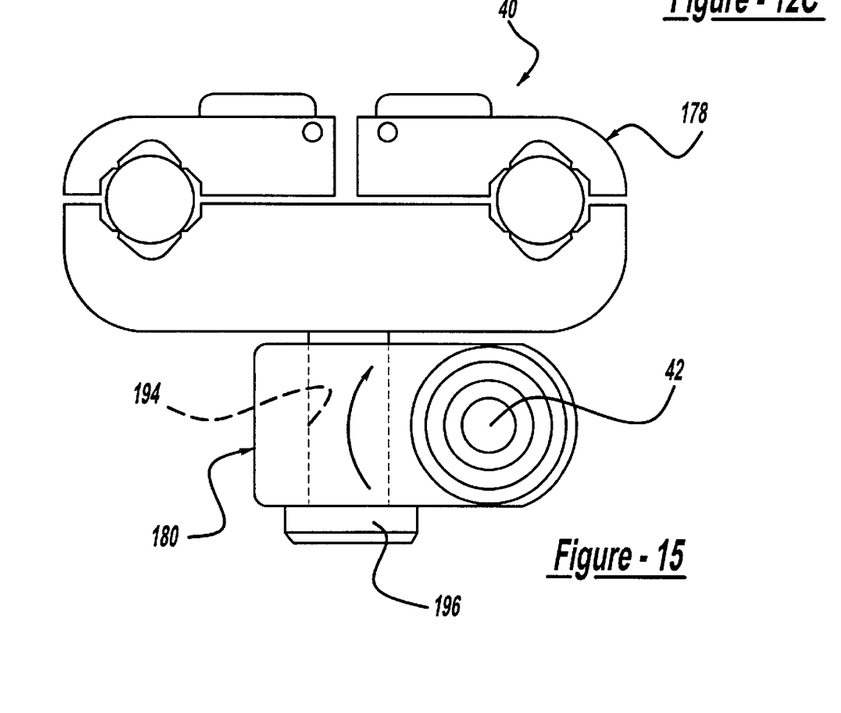
FIG. 15 is a side elevational view of the bar clamping unit and threaded rod receiving unit the compression/distraction assembly of the external fixation system according to the teachings of the preferred embodiment of the present invention.

With reference to FIGS. 13 and 15, the compression/distraction arrangement 38 of the present invention will be described. The clamping assemblies 40 of the distraction arrangement 38 each include a bar clamping unit 178 and a threaded rod receiving unit 180. The bar clamping unit 178 includes a lower portion 182 and a pair of substantially identical upper portions 184. Each of the upper portions 184 cooperates with the lower portion 182 to define an aperture 186 for receiving one of the support rods 48. The upper portions 184 each include an apertures 188 which each allow a threaded fastener 190 to pass therethrough and into an aligning threaded aperture 192 provided in the lower portion 182. Tightening of the fasteners 190 secures the support rods 48. When the bar clamping units 178 are used in tandem, a pair of the support rods 48 are non-rotatably retained in a parallel and spaced apart relationship.

The threaded rod receiving unit 180 of each of the clamping assemblies 40 includes a first aperture (not specifically shown) which is internally threaded for receiving the drive rod 42. The clamping assemblies 40 additionally include a second aperture 194 oriented substantially perpendicular to the first aperture. The second aperture 194 allows a threaded fastener 196 to pass therethrough and into an aligning internally threaded aperture 198 provided in the lower portion 182 of the bar clamping unit 178 for securing the bar clamping unit 178 to the threaded rod receiving unit 180.

When the compression/distraction arrangement 38 is incorporated into a construct, as shown in FIG. 2 for example, the threads of the apertures receiving the drive rod 42 progress in opposing directions. To operate the compression/distraction arrangement 38, the fastener 190 of a first one of the bar clamping units 178 which is associated with one of the support rods 48 must be loosened to permit the support rod 48 to slide within the aperture 186. Similarly, the fastener 190 of a second of the bar clamping units 178 which is associated with the other one of the support rods 48 must be loosened to permit the support rod 48 to slide in its aperture 186. In this manner, one of the bar clamping units 178 is permitted to translate with respect to one of the support rods 48 and the other of the clamping units 178 is permitted to translate relative to the other of the support rods 48. At this point, rotation of the drive rod 42 in a first direction causes relative movement between the clamping assemblies 40 such that they approach one another and the bone 14 is compressed. Conversely, rotation of the drive rod 42 in a second direction causes relative movement between the clamping assemblies 40 such that they diverge from one another and the bone 14 is distracted.

The ring assembly 46 of the present invention is shown in the exemplary construct of FIGS. 3A and 3B. A substantially identical ring assembly is shown and described in commonly assigned U.S. Ser. No. 09/086,256, filed Jun. 28, 1998. U.S. Ser. No. 09/086,256 is incorporated by reference as if fully set forth herein.

The foregoing discussion discloses and describes merely exemplary embodiments of the present invention. One skilled in the art will recognize from such discussion and from the accompanying drawings and claims, that various changes, modifications and variations can be made therein without departing from the spirit and scope of the invention.

What is claimed is:

1. An external fixation system for securing a first bone portion in a fixed relationship to a second bone portion by a first bone pin connected to the first bone portion and a second bone pin connected to a second bone portion, the external fixation system comprising:

a first support rod;

a threaded fastener;

a first coupling component including first and second halves cooperatively defining a clamp opening receiving the first support rod and including aligning apertures receiving the fastener; and a second coupling component including a threaded aperture for threadably receiving a threaded end of the threaded fastener such that rotation of the threaded fastener in a first direction draws together the first and second halves and secures a relative position between the first coupling component and the second coupling component.

2. The external fixation system of claim 1, wherein the second coupling component is a telescoping bone screw clamp for interconnecting the first bone pin and the first coupling component .

3. The external fixation system of claim 1, wherein the second component is configured to receive a plurality of bone pins.

4. The external fixation system of claim 3, wherein the second component includes a base and a cover secured to the base, the base including a generally cylindrical extension defining a threaded aperture receiving the threaded fastener.

5. The external fixation system of claim 3, wherein the second component includes a base and a cover secured to the base, the cover including a generally cylindrical extension defining a threaded aperture receiving the threaded fastener.

6. The external fixation system of claim 1, wherein the second component defines an aperture receiving a generally cylindrical shaft.

7. The external fixation system of claim 6, wherein rotation of the fastener in the first direction further serves to clamp the generally cylindrical shaft in the aperture of the second component.

8. The external fixation system of claim 6, wherein the first and second components include cooperating serrations to prevent relative rotation about the fastener.

9. The external fixation system of claim 1, wherein the second component includes a cylindrical post portion extending along a post axis and a mounting portion including an aperture for threadably receiving the threaded fastener, the aperture oriented perpendicular to the post axis.

10. The external fixation system of claim 9, wherein a first side of the mounting portion includes a serrated portion surrounding the aperture.

11. The external fixation system of claim 1, wherein the second component defines a pin aperture for receiving the first bone pin, the second component including an upper flange portion and a lower flange portion separated by a gap, the gap intersecting the pin aperture and whereby rotation of the threaded fastener in the first direction secures the first bone pin in the pin aperture.

12. The external fixation system of claim 1, wherein the second component defines a cylindrical shaft aperture, and further including a third component having a cylindrical shaft portion, whereby rotation of the threaded aperture in the first direction further serves to secure the cylindrical shaft portion within the cylindrical shaft aperture.

13. The external fixation system of claim 12, wherein the third component includes a mounting portion having a threaded aperture perpendicular to a shaft axis defined by the cylindrical shaft portion.

14. The external fixation system of claim 1, wherein the second coupling component includes a shaft opening receiving a shaft and first and second flange portions separated by a gap, whereby rotation of the threaded fastener in the first direction further operates to secure the shaft in the shaft opening.

15. An external fixation system for securing a first bone portion in a fixed relationship to a second bone portion by a first bone pin connected to the first bone portion and a second bone pin connected to a second bone portion, the external fixation system comprising:

a first support rod for interconnection to the first bone pin;

a second support rod for interconnection to the second bone pin;

a compression/distraction mechanism including first and second support rod clamping units, an externally threaded drive rod and first and second rod receiving units, the first and second rod clamping units each defining a pair of apertures receiving the first and second support rods such that the longitudinally extending axes of the first and second support rods are in a spaced apart relationship, the first and second drive rod receiving units attached to the first and second support rod clamping units, respectively, the threaded drive rod rotatably received by both of the first and second drive rod receiving units such that rotation of the drive rod in a first direction causes relative movement between the first and second support rod clamping units so that they approach one another and rotation of the drive rod in a second direction causes relative movement between the first and second support rod clamping units so that they diverge from one another.

16. The external fixation system of claim 15, wherein the first and second drive rod receiving units are removably attached to the first and second support rod clamping units, respectively.

17. The external fixation system of claim 15, both of the first and second rod clamping units include a lower portion and at least one upper portion which cooperate to define the pair of apertures receiving the first and second support rods.

18. The external fixation system of claim 17, wherein the first and second apertures are parallel to one another and spaced apart.

19. The external fixation system of claim 17, wherein each of the lower portions define an aperture receiving a fastener for securing a respective one of the first and second drive rod receiving units.

20. An external fixation system for securing a first bone portion in a fixed relationship to a second bone portion, the external fixation system comprising:

a plurality of generally cylindrical rods;

a plurality of threaded fasteners;

a plurality of bone pins;

a first coupling component having first and second portions defining a cylindrical shaft opening receiving a first cylindrical rod and including aligning apertures generally perpendicular to the cylindrical shaft opening for non-threadably receiving one of the plurality of threaded fasteners;

a second coupling component including first and second flange portions separated by a gap and a cylindrical shaft opening, the gap intersecting the cylindrical shaft opening, the first and second flange portions defining first and second aligning fastener apertures, at least one of the first and second aligning fastener apertures for receiving one of the plurality of threaded fasteners; and a third coupling component defining a pin aperture for receiving one of the plurality of bone pins, the third coupling member including a fastener aperture for receiving one of the plurality of threaded fasteners;

wherein the second coupling component is selectively secured to the first coupling component by a first of the plurality of threaded fasteners passing through the aligning apertures and threadable engaging the at least one of the first and second aligning apertures of the second component such that rotation of the first threaded fastener in a first direction clamps the first cylindrical rod within the cylindrical shaft opening of the first coupling component, clamps a cylindrical shaft within the cylindrical shaft opening of the second coupling component and secures a relative position between the first and second coupling components;

wherein the third coupling component is selectively secured to the first coupling component by the first of the plurality of threaded fasteners passing through the aligning apertures and threadably engaging the fastener aperture of the third coupling component such that rotation of the first threaded fastener in the first direction clamps the first cylindrical rod within the cylindrical shaft opening of the first coupling component and secures the relative position between the first and third coupling components.

* * * * *